United States Patent [19]

Brossel

[11] Patent Number: 4,747,414
[45] Date of Patent: May 31, 1988

[54] INSTRUMENT FOR BONE MARROW PUNCTURE

[75] Inventor: 'Rémy Brossel, Paris, France
[73] Assignee: Biologie et Industrie S.A.R.L., Chaumont, France
[21] Appl. No.: 928,245
[22] PCT Filed: Feb. 20, 1986
[86] PCT No.: PCT/FR86/00052
§ 371 Date: Oct. 20, 1986
§ 102(e) Date: Oct. 20, 1986
[87] PCT Pub. No.: WO86/04805
PCT Pub. Date: Aug. 28, 1986

[30] Foreign Application Priority Data

Feb. 20, 1985 [FR] France ............................ 85 02452

[51] Int. Cl.⁴ ............................................. A61B 10/00
[52] U.S. Cl. ..................................... 128/754; 128/763; 604/87; 604/157
[58] Field of Search ................ 128/749, 751–754, 128/760, 763, 765, 770, 305, 310; 604/82, 87, 89, 156, 157, 136, 200, 229, 416, 900

[56] References Cited

U.S. PATENT DOCUMENTS

| 3,656,472 | 4/1972 | Ben Moura | 128/763 |
| 3,815,605 | 6/1974 | Schmidt et al. | 128/305 |
| 4,134,512 | 1/1979 | Nugent | 128/764 |
| 4,239,040 | 12/1980 | Hosoya et al. | 128/769 |
| 4,517,978 | 5/1985 | Levin et al. | 604/136 |

FOREIGN PATENT DOCUMENTS 3108766 9/1982 Fed. Rep. of Germany .
1190905 4/1959 France ............................ 128/749

Primary Examiner—Kyle L. Howell
Assistant Examiner—Randy Citrin
Attorney, Agent, or Firm—Fleit, Jacobson, Cohn & Price

[57] ABSTRACT

The invention relates to an instrument for bone marrow puncture comprising a sampling needle (10) fused to a piston which can be displaced within a piston barrel (4), a mechanism (6) for releasing the piston from a first position, at which the needle is entirely withdrawn within the interior of the anterior part of the said piston barrel, to a second position at which the extremity of the needle is projected to the outside. The stroke of the piston is sufficient for the needle to pierce the bone and reach the region of the bone marrow where sampling is to be carried out, when the anterior part (32) of the instrument is placed and maintained at the height of the appropriate bone. The posterior part of the piston barrel defines a closed chamber (16) for the collection of the marrow sample aspirated into this chamber under the effect of the negative pressure generated by the displacement of the piston from the first to the second position.

12 Claims, 1 Drawing Sheet

INSTRUMENT FOR BONE MARROW PUNCTURE

BACKGROUND OF THE INVENTION

The red, or haemopoietic, bone marrow is a semi-liquid organ, of about 5 liters capacity and contained in the bones. The marrow manufactures the cells which subsequently circulate in the blood after having passed into the "circulating sector", i.e. the blood volume available in the veins and arteries.

For several decades "bone marrow punctures" or "medullary punctures" have been performed in order to remove a sample of haemopoietic marrow required for the conduct of biological examinations. These examinations are required, in particular, by haematologists in cases of serious abnormalities of blood cells, primarily in cases of leukaemias, which are medullary diseases. The equipment used is, in general, specifically designed for this type of puncture, essentially because, on the one hand, of the semi-liquid nature of the organ sampled, the marrow, and, on the other, of the need to reach the marrow by passing through another, hard organ, the bone. Only the bone marrow presents these two characteristics.

The equipment usually includes trocars capable of passing through the sternum, from which comes the name, very frequently used, of sternal puncture. In France, a Mallarmé trocar is usually chosen, one which can be pushed manually through the bone. The internal diameter of this trocar varies from 8 to 20 hundreths of a millimetre and its length is sufficient to pass through the thickness of the hard bone (about 1 cm)—or "compact"—which surrounds the marrow. One speaks of passing through the cortex to reach the medullar. Once the bevelled end of the trocar is located in the medullary space, it is necessary to aspirate gently with a syringe in order to withdraw 0.5 to 2.0 ml of marrow; the latter is, in fact, quite viscous and the medullary space is septated into many spaces by quite fragile lamella of bone.

The marrow is collected in a syringe, in the presence of an anticoagulant in order to avoid the formation of a clot. Subsequently, both syringe and trocar are withdrawn. Only the trocar is cleaned, sterilised and reused. From the syringe a drop of marrow is deposited on a slide. The drop is spread, dried and sent to the laboratory where it will be dyed and examined under a microscope.

A result of carrying out what has just been described is that the sampling of marrow constitutes a traumatic experience for the patient. To this major disadvantage, unavoidable to this day, is added the frequently encountered difficulty of the reproducibility of sampling.

The aim of the invention is to remedy these difficulties, at least in part, and, in particular, to provide sampling equipment for bone marrow which will be both less traumatising for the patients and more reliable in the hands of the physician or technician, and at a price reduced to the point where it becomes "disposable", thus eliminating all the problems of sterilisation which, at present, has to be repeated between successive uses of the equipment.

SUMMARY OF THE INVENTION

The instrument according to the invention consists of a sampling needle passing through and forming part of a piston, the piston being free to move within the interior of the barrel of the piston or tube between a first position and a second position, characterised in that the piston is maintained in the first position against the action of devices exerting a force tending to displace it to the second position, by restraining devices which can be controlled from the outside to release the piston so that it may move to the second position.

in the first position the needle is entirely retracted within the interior of the anterior part of the piston barrel, and in that the stroke of the piston is such that, when the anterior part of the instrument is placed and maintained in position by the technician, directly or by the intermediary of an external system of support harnessed to the instrument against the body of the patient or at a defined distance from the body of the patient, at the height of the bone which has to be pierced by the needle, the end of the needle should be able to project from the barrel of the piston at its anterior end, in particular by piercing a capsule or something similar, and be able to pass through the thickness of the bone and reach the region of the marrow where the sample is to be taken, when the piston is released by the said external control and, the posterior part of the barrel of the piston, on the other side of the piston, defines a closed chamber for receiving the sample of marrow taken and aspirated into the chamber, as a result of the negative pressure created by the displacement of the piston from the first to the second position.

It is obvious that the means used to displace the piston to the second position must exert a sufficient force to ensure the piercing of the sternum or another bone giving access to the marrow and give the needle access to the medullary space. The means should preferably be elastic in nature. Advantageously, they are constituted by a spring working in traction.

A preferred embodiment of the instrument of the invention includes one or several compartments, separate from the collection chamber but which can be connected to it. This or these compartment(s) may contain various reagents, liquid or solid, such as preservation media. In a preferred form of the instrument according to the invention, the separation between the collection chamber and such a compartment consists of a thin disc or film, of aluminium or plastic material for example, capable of being broken under the effect of the negative pressure created by the displacement of the piston from the first position to the second position. This separate compartment may contain, for example, reagents which may thus be mixed instantaneously with the sample of marrow which is aspirated into the chamber.

The elastic devices intended to displace the piston from the first position to the second position are advantageously constituted by a spring working in traction. The externally controlled devices for releasing the piston which is subject to the action of the said spring are constituted, for example, of stopping pins or catches against which the piston rests, these stopping pins and catches being retractable into or against the interior wall of the piston barrel, and being under external control. This latter may consist of any appropriate means, for example, an external, mechanical device such as a lock-release system, attached to or capable of being attached to the body of the system. This release system is mounted, for example, in a system provided with a housing into which the entire system can be fitted. This external system includes advantageously, in addition to this housing, a handle suitably placed with regard to the instrument according to the invention so as to permit the application of the anterior part or the corresponding anterior edges of the system to the appropriate part of the body of the patient in a way which ensures correct contact, directly to the skin, and, finally, a triggering device, connected to the said retractable stopping pins by the intermediary of an appropriate kinematic device. This ergonomic handle must make it easy to take hold of the instrument, leave one finger free for triggering and ensure manual dampening of the recoil of the piston.

Advantageously, the instrument according to the invention forms a "cartridge" which may be housed in the support system, this latter system being, in addition, equipped with means which enable mechanical or other contact to be made between the braking mechanism and the control mechanism, for example, by the trigger mentioned above.

The instruments of the invention allow the collection of marrow in the medullary space to be mechanised and/or automated. The invariability in all individuals of the thickness of the bone to be pierced in order to reach the marrow also makes it possible to obtain or collect samples of constant volume and which are likely to be representative of the haemopoietic marrow since the dimensions and strength of the elastic or other devices used are also constant from one cartridge to another.

Thus, instruments can be made which reduce the traumatising aspect of the operation of taking a bone marrow sample to a minimum. The instrument according to the invention meets two of the aims of the invention, in particular, the two component parts of sternal puncture are carried out more quickly (piercing of the bone and aspiration of the marrow) and the conditions of the operation are improved for the practitioner himself as is the reproducibility of sampling, contact with the patient being mediated by the end of the instrument according to the invention (or by the parts of the device housing this instrument and including the controls) on its being applied to the sternum of the patient. The task of the physician or technician is thus essentially limited to the triggering of the movement of the piston and the sampling needle which is joined to it. In brief, the mechanisation of the operation leads to samples of reproducible quality.

A further advantage of the instrument according to the invention lies in its low cost. In fact, the essential elements of this instrument, consisting of the sampling needle, the piston joined to it and the barrel of the piston, can be constructed of inexpensive materials. In their most advantageous form, the instruments according to the invention are constituted of cartridges which are intended to be used only once. In other words, after use they can be thrown away.

The barrel of the instrument, including the chamber mentioned above, may also be used to preserve the sample during the time taken to transfer it to the laboratory. Advantageously, the barrel is constructed in two parts separable from each other, for example, by a threaded joint which offers the possibility of storing the contents in the chamber until the analyses are performed.

Additional characteristics of the invention will be presented as part of the description which follows of preferred embodiments of the instrument according to the invention, made in conjunction with the diagrams in which:

DESCRIPTION OF THE PREFERRED EMBODIMENT

Figure 1:
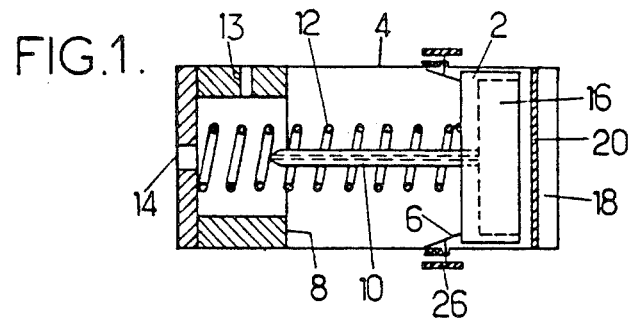
FIG. 1 presents a transverse section of an embodiment of the instrument according to the invention, of the cartridge type, in which the piston is maintained in the "first position".

FIG. 1 shows the essential elements of the sampling instrument according to the invention. It consists of a piston 2 capable of being displaced within the interior of the barrel 4, generally tubular, between the above-mentioned first and second positions, defined respectively by the stopping pins or catches 6 and by a stop 8. The piston is maintained in the first position by means of the said stopping pins and catches, which are shown in FIG. 1 to be projecting from the interior walls of the barrel towards the interior. The needle 10, including its suitably bevelled tip, is in the rest position within the barrel.

Retraction of the stopping pins or catches into the interior of the wall of the barrel (or retraction of the catches towards the interior surface of the barrel), leads to the piston, and the hollow needle 10 joined to it, being impelled towards the second position by the intermediary of a spring 12 working in traction, the movement of the piston towards the second position being interrupted when it reaches the said stop 8. Preferably, a lateral orifice 13 is provided in the piston barrel, beyond the second position of the piston, through which air may escape which otherwise would counteract the thrust of the piston.

The stroke of the piston is calculated so that the attached needle is able to traverse the lower part of the barrel (initially closed by a percussion cap 14 which the needle pierces) and the bone, and comes to rest in the bone marrow where the sample is to be taken, when the said instrument has been placed against the sternum of the patient and held in that position while the piston and needle are displaced by the action of the traction spring 12. It is obvious that the force of this spring has to be calculated so that the needle is indeed able to pierce the sternum.

As is also evident in FIG. 1, the piston is advantageously hollow and it defines in the part of the barrel facing a chamber 16 for the collection of the marrow sample which is aspirated into this chamber by the effect of the negative pressure created when the piston is displaced from the first to the second position.

FIG. 1 also shows the existence of a distinct compartment 18, which can be connected to chamber 16. In the embodiment shown, chamber 16 and the compartment 18 are separated by film 20 which may be broken, in particular, as a result of the negative pressure created when the piston moves from the first to the second position under the action of the spring 12.

Figure 2:
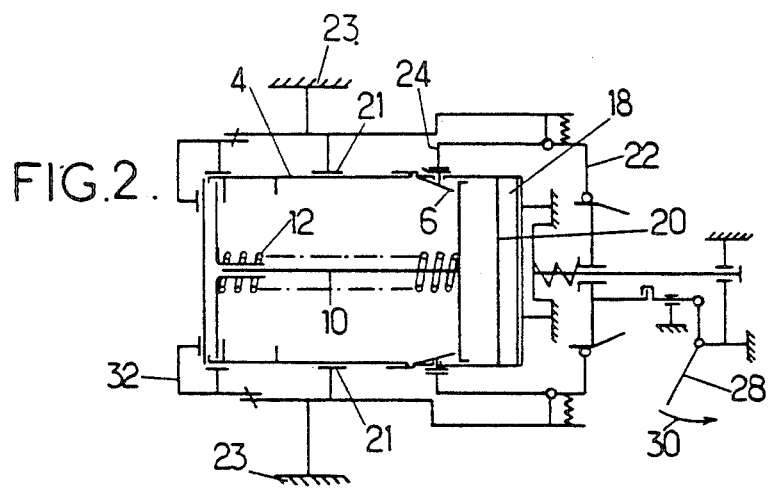
FIG. 2 presents a cartridge of the same type in combination with a supporting device or receiver for the cartridge, this supporting device being equipped with controls to trigger the release of the piston, the latter, however, being still retained in the "first position".
Figure 3:
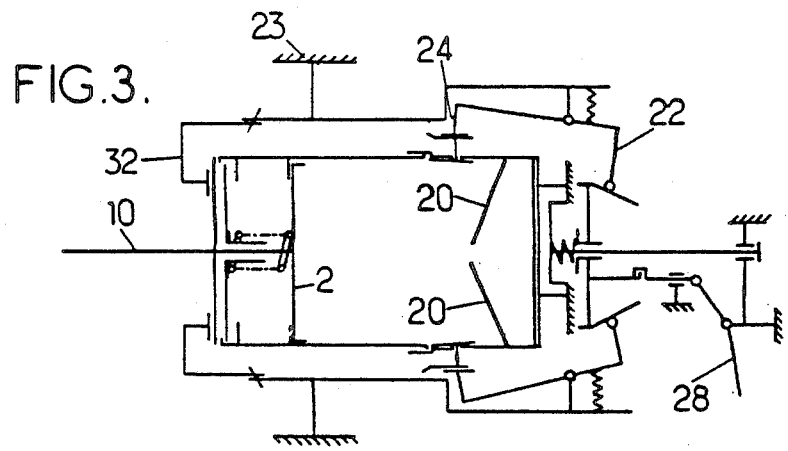
FIG. 3 is a scheme of the same system, after release of the piston which is now drawn in the "second position".

The instrument shown in FIG. 1, which is presented in the form of a cartridge, is designed so that it can be integrated into a supportng system shown schematically in FIGS. 2 and 3 and includes, in particular, the partitioning elements 21, specifying a housing for the cartridge, and control units connected to the stopping pins or catches which block the piston in the first position, and supporting devices belonging to the ergonomic handle (not shown, except for the parts schematised in 23). This mounting comprises, in particular, connecting the control units schematised in 22 to the stopping pins or catches 6 as shown schematically in 24. Moreover, it will be noted in this respect that, before being connected, the stopping pins or catches 6 of the cartridge can be maintained in place, for example, by the intermediary of a small disc 26 of elastic material, in particular rubber or another similar material, this small disc being removed or ejected when the said cartridges are introduced into the housing of the supporting device.

The unit controlling the withdrawal of the stopping pins or catches 6 from the interior may pass, for example, via a triggering mechanism 28, which may be activated, for example, in the direction indicated by the arrow 30.

FIG. 3 shows the conditions under which the triggering mechanism is released by the trigger 28. The withdrawal of the stopping pins has resulted in the rapid movement of the piston and the needle joined to it to the second position. It is, of course, obvious that in the design under consideration, the length of the piston is such that the length of that part of the needle projecting beyond the surface 32, which is the point of application of the system to the sternum of the patient, corresponds to the distance the needle needs to penetrate in order that its extremity becomes lodged in the marrow to be sampled.

FIG. 3 also shows the partition film 20, which initially separated the chamber 16 from the compartment 18, which is broken as a result of the negative pressure created as a consequence of the brisk movement of the piston from the first to the second position brought about by spring 10. It is easy to see that the instrument according to the invention thus leads to mixing in situ of the marrow aspirated into chamber 16 and a liquid initially present in compartment 18. It is, of course, obvious that the instrument can be put to other uses, which involve, for example, the mixing of the isolated marrow with dry substances deposited on the membrane 20 or even (when no membrane is present) on the walls or top of the chamber, at the end of the barrel opposite to that through which the needle projects.

It will be obvious that generally the length of the needle, the volume of the piston barrel and the internal volume of the chamber are calculated so as to guarantee that the desired quantity of marrow sample is taken.

For example, suitable dimensions for the essential parts of the instrument or the cartridge are as follows:

stroke of the piston: corresponds to the projecting length required for penetration of the needle into the sternum: 15 mm internal cross-section of cartridge (usual values): 2 to 4 $cm^2$ internal diameter of hollow needle (usual values): 0.05 to 0.30 mm.

It is obvious that any other control unit may be used as well as the one described. The system of stopping pins or catches may be replaced by electromechanical or electromagnetic control units. The energy required to displace the piston from the first to the second position may be supplied by other means, pneumatic devices for example, or by a force which is opposed by a pressure of air maintained in the internal space to be traversed by the piston, the mechanism being triggered by releasing the air pressure, etc.

The supporting device may be constructed from any model. Advantageously, it includes an ergonomic handle (not shown), making for easy handling of the equipment, for effective application of the surface 32 to the sternum of the patient, and allowing manual dampening of the recoil of the piston when the latter moves rapidly from the first to the second position as a consequence of the stopping pins or catches having been withdrawn by the control device.

The system is thus ready to be used.

After being released, the path through which the piston moves is sufficient for the needle to pierce the percussion cap 14, pass through one centimetre of compact bone in the adult and come to rest at a depth of about 0.5 cm in the marrow. The negative pressure created by the movement of the piston produces the back flow through the needle of 0.5 to 1.0 $cm^3$ of marrow and brings about the separation or breaking of the membrane or metallic disc 20.

The applications of this system are numerous. For example, the marrow which flows back into chamber 16 can be mixed with a liquid culture medium, heparinized or treated with an anticoagulant if necessary, or, mixed with a specific antibody initially attached to the membrane and dissolved by the medium. The antibody is intended to detect particular membrane antigens or foreign cells in the marrow, for example.

The sample may be shaken in order to mix it well before being sent to the laboratory; it can be preserved for several hours in culture medium at room temperature. This treatment ensures the preservation of the membrane antigens necessary for the detection of foreign cells in the marrow or for the study of populations of strain or differentiated cells. As examples of other uses for which the instrument according to the invention may be employed, the following will be mentioned:

the direct or delayed transport of a sample to the laboratory which has been simply collected in the presence of anticoagulant, preservation of the marrow sample collected in an appropriate medium, treatment of the sample taken in the interior of the apparatus itself, then re-injection of the mixture (a case in which the system will need to be modified to allow the piston to be returned from the "second position" to the "first position"), the labelling of certain categories of medullary cells by whatever means, enzymatic, immunological, radioactive etc . . . , study of abnormal or foreign cells in the marrow, the transfer to a measuring apparatus such as a cytometer in liquid flow or a centrifuge or a system of sorting, and even fixation and incorporation, in the interior of the apparatus.

As is obvious and, furthermore, clear from what has been written, the invention is not at all limited to those modes of application and the embodiments of the invention which have been given particular attention in the text; on the contrary, it embraces all possible variants.

I claim:

1. An instrument for performing a bone marrow puncture, comprising:
    (a) a barrel having a central axis extending between an anterior end of said barrel and a closed posterior end of said barrel;

(b) a piston located in a first axial position within said barrel and movable anteriorly along said axis away from said first axial position to a second axial position; said closed posterior end of said barrel defining, with said piston, a first closed chamber within said barrel posterior to said piston;

(c) a hollow needle that is within said barrel, is fixed to said piston, and extends anteriorly along said axis away from said piston; said needle having open anterior and posterior ends; said posterior end of said needle being in fluid-flow communication with said first closed chamber so that said anterior end of said needle is also in fluid-flow communication with said first closed chamber through said needle;

(d) releasable means for restraining movement of said piston within said barrel along said axis away from said first axial position; and (e) means for urging said piston to move anteriorly within said barrel a first predetermined distance along said axis from said first axial position to said second axial position so that said anterior end of said needle is urged to move: (i) said first predetermined distance along said axis and (ii) a second predetermined distance along said axis outwardly of said anterior end of said barrel; whereby said open anterior end of said needle can pierce a bone adjacent to said anterior end of said barrel and can move into marrow of said bone; and whereby said first closed chamber, defined by said piston and said closed posterior end of said barrel, becomes enlarged as said piston moves anteriorly, thereby reducing pressure in said first closed chamber and causing said marrow to be aspirated into said first closed chamber through said hollow needle and its open ends.

2. The instrument of claim 1, wherein said urging means (e) comprises a spring working in traction between said piston and said anterior end of said barrel.

3. The instrument of claim 2, wherein said releasable restraining means (d) comprises a retractable, externally controlled catch within said barrel holding said piston in said first axial position.

4. The instrument of claim 2, wherein said releasable restraining means (d) comprises a retractable, externally controlled pin within said barrel holding said piston in said first axial position.

5. The instrument of claim 2 which further comprises a step for said piston within said barrel at said second axial position.

6. The instrument of claim 1, wherein said open anterior end of said needle is within said barrel until it is urged to move outwardly of said anterior end of said barrel by said urging means (e).

7. The instrument of claim 6, wherein said anterior end of said barrel is covered by a cap until said open anterior end of said needle is urged to move outwardly of said anterior end of said barrel and through said cap by said urging means (e).

8. The instrument of claim 1, wherein said first closed chamber is connected to a second closed chamber that is within said barrel, is posterior to said piston, and contains a solid or liquid reagent.

9. The instrument of claim 8, wherein said first and second closed chambers are connected by a frangible barrier which is broken by a reduction in pressure in said first closed chamber caused by said piston moving anteriorly within said barrel by said first predetermined distance along said axis.

10. The instrument of claim 9, wherein said frangible barrier is an aluminium or plastic film.

11. The instrument of claim 1, wherein said barrel has a lateral pressure-relief orifice therein which is located anteriorly of said second axial position of said piston.

12. The instrument of claim 1, wherein said barrel is generally tubular.

* * * * *